(12) United States Patent
Al-Khattaf et al.

(10) Patent No.: US 9,586,873 B2
(45) Date of Patent: Mar. 7, 2017

(54) METHOD FOR THE SELECTIVE PRODUCTION OF PARA-DIALKYLBENZENES

(71) Applicant: King Fahd University of Petroleum and Minerals, Dhahran (SA)

(72) Inventors: Sulaiman Saleh Al-Khattaf, Dhahran (SA); Syed Ahmed Ali, Dhahran (SA); Abdullah Mohammed Aitani, Al-Khobar (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 252 days.

(21) Appl. No.: 14/294,774

(22) Filed: Jun. 3, 2014

(65) Prior Publication Data

US 2015/0344384 A1 Dec. 3, 2015

(51) Int. Cl.
*C07C 2/86* (2006.01)
*C07C 6/12* (2006.01)

(52) U.S. Cl.
CPC .............. *C07C 2/864* (2013.01); *C07C 6/123* (2013.01); *C07C 2529/40* (2013.01)

(58) Field of Classification Search
None
See application file for complete search history.

(56) References Cited

U.S. PATENT DOCUMENTS

| | | | | |
|---|---|---|---|---|
| 3,755,483 A | * | 8/1973 | Burress | B01J 20/3408 502/77 |
| 4,100,217 A | * | 7/1978 | Young | C07C 2/66 585/467 |
| 4,379,761 A | * | 4/1983 | Olson | B01J 21/08 502/214 |
| 4,524,230 A | * | 6/1985 | Haensel | C07C 2/76 208/112 |
| 4,613,717 A | | 9/1986 | Ishida et al. | |
| 5,675,047 A | * | 10/1997 | Beck | B01J 29/40 502/63 |

FOREIGN PATENT DOCUMENTS

EP 0289691 B1 8/1992

* cited by examiner

*Primary Examiner* — In Suk Bullock
*Assistant Examiner* — Alyssa L Cepluch
(74) *Attorney, Agent, or Firm* — Oblon, McClelland, Maier & Neustadt, L.L.P.

(57) ABSTRACT

A method is disclosed for selective simultaneous production of para-xylene, para-ethyltoluene and para-diethylbenzene from a reactant stream containing ethylbenzene and methanol, as an alkylating agent. The process comprises alkylation of the feedstock in a fluidized-bed rector under alkylating conditions, over a modified ZSM-5-based catalyst to produce streams containing above 95% para-isomers of dialkylbenzenes. The method also includes the steps of multilayer silylation to achieve simultaneous selectivity of the para-isomers of dialkylbenzenes.

7 Claims, 2 Drawing Sheets

METHOD FOR THE SELECTIVE PRODUCTION OF PARA-DIALKYLBENZENES

BACKGROUND OF THE INVENTION

Technical Field

The present disclosure relates to a method for the selective production of para-isomers of dialkylbenzenes using a ZSM-5-silylated catalyst, a method for making the ZSM-5-silylated catalyst, and a method for the selective production of para-isomers where the selectivity of the para-dialkylbenzene isomers is at least 95 wt. % para-selectivity.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Xylenes encompass three isomers, namely ortho-, meta- and para-, of dimethylbenzene. para-Xylene is the principal precursor to terephthalic acid and dimethyl terephthalate, both monomers used in the production of polyethylene terephthalate plastic bottles and polyester clothing. 98% of para-xylene production, and half of all xylenes, is consumed in this way. The thermodynamic equilibrium yields only about a quarter of para-xylene, whereas its demand is much higher.

Ethyltoluenes also have three isomers namely ortho-, meta- and para-. The para isomer is used for the production of an important monomer, para-methylstyrene, by dehydrogenation. Poly(para-methylstyrene) has advantage over polystyrene due to its low density. It also has high glass transition temperature and flash point compared to polystyrene, therefore, it can have more potential application in the area of flame retardancy or ignition resistance. Packages made from poly(para-methylstyrene) are preferred for food packages which are subjected to high temperatures.

Diethylbenzenes have three isomers namely ortho-, meta- and para-. The para isomer is industrially more important than the other two isomers. It is a high-value chemical having immense industrial importance by virtue of its utility as a desorbent in the selective recovery of para-xylene from mixed xylene stream, by well known "Parex" adsorption process innovated by UOP, A Honeywell Company (USA).

Dialkylbenzenes have been traditionally synthesized using alkylation catalysts like $AlCl_3$, HF, $BF_3$ etc. However, the conventional catalyst is not selective to the para-isomer. Isomers of ortho-, meta- and para-dialkylbenzene can result in a thermodynamic equilibrium concentration. These isomers have very close boiling points to each other and the relative volatility is nearly one. Separation is difficult and is quite expensive. Moreover, due to strong acidity, disposal of catalyst causes serious environmental pollution apart from corrosion of equipment during operation of the process. Another approach for producing para-xylene (p-X), para-ethyltoluene (p-ET), and para-diethyl benzene (p-DEB) is through adsorptive separation of para-isomer from mixed diethyl benzene isomers, which are produced during ethylbenzene/styrene manufacture.

Solid acid catalysts, particularly zeolites have replaced the earlier $AlCl_3$, HF, $BF_3$ type catalysts. ZSM-5 is a type of zeolite catalyst which is used as solid acid catalyst having unique feature of shape selectivity. The pores of this sort of zeolites have a uniform aperture. Therefore, hydrocarbons smaller than the pore dimensions are adsorbed and larger hydrocarbons are rejected. ZSM-5 is frequently referred to as a "molecular sieve". The ZSM-5 zeolite catalyst is characterized by its selectivity, being able to satisfy the needs for high selectivity to products of different molecules, but it still falls short of expectation in respect of isomers of same kind of product.

Various techniques to enhance shape selectivity of medium pore aluminosilicates have been reported. U.S. Pat. Nos. 4,086,287; 4,094,921 and 4,117,024 describe catalytic processes for selective ethylation of monoalkylbenzene (toluene, ethylbenzene) to produce p-X, p-ET, and p-DEB, using ZSM-5 catalyst modified with oxides of phosphorus, antimony, boron, magnesium and/or steaming and coking. U.S. Pat. Nos. 4,117,026 and 4,128,592 describe catalytic processes for the selective production of para dialkyl substituted benzenes using aluminosilicate zeolite modified with oxides which are difficult to reduce and further modified by coking. Catalysts and processes for selective production of para-dialkyl substituted benzenes have also been described in U.S. Pat. Nos. 4,379,761 and 4,465,886.

Enhancement of para-selectivity, (the fraction of para-isomer in a mixture of dialkyl aromatics), by treatment with organosilicon compound has been reported. It is carried out by contacting the zeolite with organosilicon compound, separation/removal of solvent (if used), and calcination of zeolite to deposit silica or polymeric silica as a layer on the zeolite. The efficiency of silica deposition in order to enhance the selectivity of the zeolite depends on the nature or the kind or the type or the molecular structure of the organosilicon compound employed. The efficiency of silica deposition also depends on the temperature of silylation, the solvents or the carrier for the organosilicon compound, the method or procedure adopted for the selectivation.

Silylation can be carried out in vapor phase or liquid phase. The zeolite is impregnated with an organosilicon compound dissolved or dispersed in a carrier or solvent followed by calcination of such treated zeolite in an oxygen containing atmosphere under conditions sufficient to remove organic material therefrom and deposit siliceous material on the zeolite. Such silylation may result in deposition of at least 1% by weight of siliceous material on the catalyst or zeolite.

Examples of various patents, which teach ex-situ selectivation of zeolites to enhance para-selectivity are U.S. Pat. No. 3,698,157, U.S. Pat. No. 4,002,697, U.S. Pat. Nos. 4,127,616 and 4,402,867. Silica modified catalysts employed for the purpose were based on zeolites like ZSM-5, ZSM-11 or ZSM-21, having surface deactivated by reaction with compounds of nitrogen or silicon, i.e. phenyl carbazole or dimethyldichlorosilane, (which are sufficiently large as to be unable to penetrate pores of crystalline aluminosilicate) followed by calcination. When ex-situ silylation process is repeated more than once, the procedure is referred to as 'multiple silylation' in which the zeolite is calcined after each impregnation of organosilicon compound.

While the above mentioned art is of interest, there is no suggestion of simultaneously enhancing the para-selectivity of dialkylbenzenes by its utilizating in short contact time fluidized-bed reactor. There is also no suggestion of multiple silylation of ZSM-5-based catalyst for ethylbenzene alkylation in the presence of methanol. Therefore, it would be a significant advance and improvement in the art through such a practical method using such modified catalyst.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

One embodiment of the present disclosure includes a method for the production of para-isomers of dialkylbenzenes.

In another embodiment the method includes contacting a silylated solid catalyst in fluidized form and a reactant in vapor form to alkylate a benzene present in the reactant in a fluidized-bed reactor.

In another embodiment the silylated solid catalyst is obtained by silylating a zeolite with tetraethyl orthosilicate to form a silylating agent.

In another embodiment the silylating agent is selectively deposited on the catalyst surface prior to the injection of a reactant feedstock into the fluidized-bed reactor.

In another embodiment the para-isomer of a dialkylbenzene is at least one para-isomer selected from the group consisting of para-xylene, para-ethyltoluene and para-diethylbenzene.

In another embodiment the contacting forms a mixture of para-dialkylbenzenes para-xylene, para-ethyltoluene and para-diethylbenzene In another embodiment the para-isomers are produced from the reactant feedstock comprising a feed of either ethylbenzene or ethylbenzene and methanol.

In another embodiment the catalyst is a modified aluminosilicate zeolite ZSM-5-based catalyst.

In another embodiment the selectivity of para-xylene, para-ethyltoluene and para-diethylbenzene among dialkylbenzene isomers is at least 95 wt. % para-selectivity.

In another embodiment the flow of ethylbenzene and methanol are combined in a molar ratio of 1:0.1 to 1:5.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
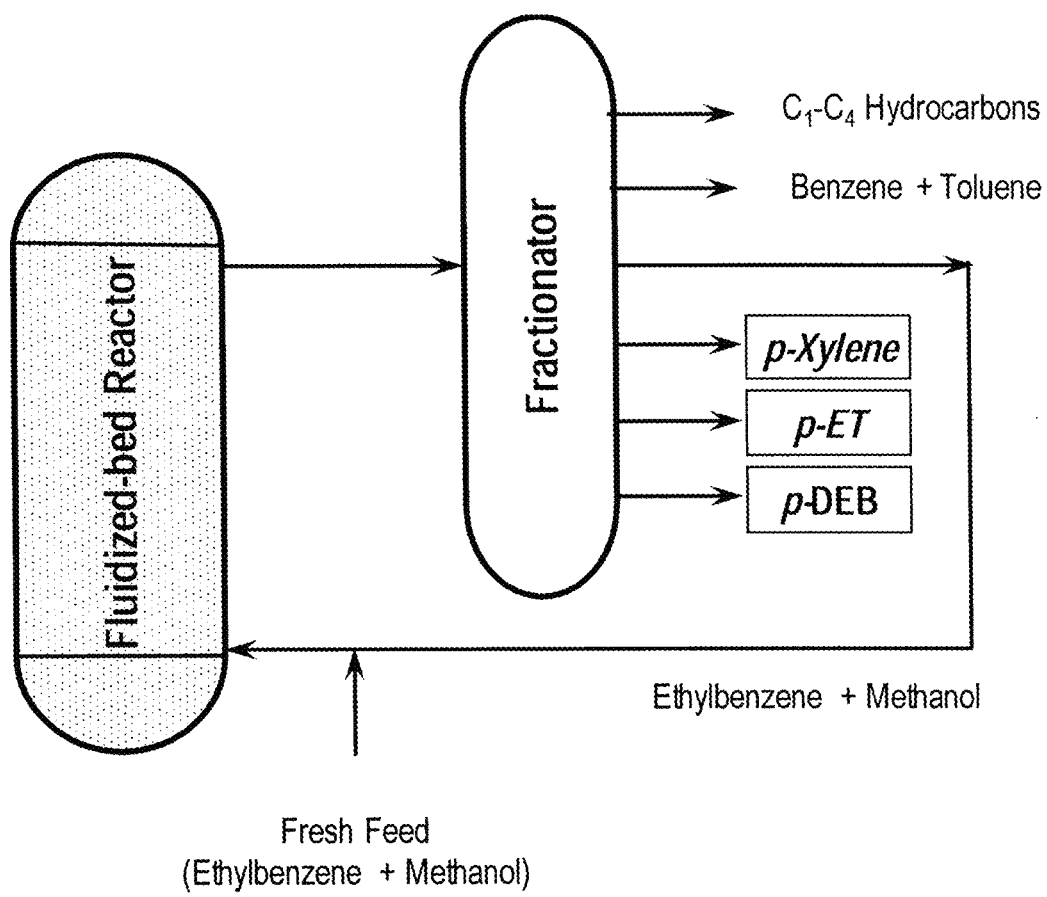
FIG. 1 is a flow diagram illustrating steps in a method for simultaneously producing p-X, p-ET, and p-DEB.

Referring now to the drawings, wherein like reference numerals designate identical or corresponding parts throughout the several views.

This disclosure is related to the production of three important dialkylaromatics from an aromatic compound and an alcohol. More specifically the present invention relates to a process for simultaneous selective production of para-xylene (p-X), para-ethyltoluene (p-ET) and para-diethylbenzene (p-DEB) using a reactant containing ethylbenzene with methanol as an alkylating agent, and any mixtures thereof using a modified ZSM-5-based catalyst.

A method is disclosed to simultaneously enhance the production of p-X, p-ET, and p-DEB using ZSM-5 based catalyst modified by organosilicon compound in a fluidized-bed reactor. A method is disclosed for selective production of p-DEB and p-ET from a reactant stream containing ethylbenzene with methanol as an alkylating agent. The process comprises alkylating the feedstock in a fluidized-bed reactor over a modified ZSM-5-based catalyst to produce a stream containing high-purity p-X, p-ET, and p-DEB with at least 95 wt. % para-selectivity.

In another embodiment the method can be performed in a reactor having a reaction chamber with an impeller. The impeller provides a fluidized-bed of catalyst particles as well as intense gas mixing inside the reactor. A mixture of ethylbenzene and methanol was used as coke precursor and selectively deposited on the catalyst surface at a selected reaction temperature, prior to the injection of the reactant feedstock in a molar ratio of 1 to 6. The catalysts are selected and formulated to remain stable under operating conditions (e.g., molar ratio of ethylbenzene to methanol, catalyst amount).

The molar ratio of ethylbenzene to methanol can be controlled such that the composition of product gas contains only negligible amount of cracking products (e.g., $C_2H_4$, $C_6H_6$).

In the present invention, p-X, p-ET, and p-DEB can be produced with a very high selectivity, by alkylation. The selectivity for p-X, p-ET, and p-DEB (among the dialkylbenzene isomers) is >95%, which makes it suitable for commercial purpose.

In one embodiment a zeolite based catalyst can be used. Zeolite based catalysts include but are not limited to ZSM-5, ZSM-11, ZSM-12, ZSM-22, or ZSM-23. Preferably the ZSM-5 catalyst is used. The ZSM-5 catalyst undergoes a chemical liquid deposition process in which the ZSM-5 catalyst is suspended in a solvent such as an alkane. The alkane is selected from a $C_1$-$C_6$ group including but not limited to methane ($CH_4$), ethane ($C_2H_6$), propane ($C_3H_8$), butane ($C_4H_{10}$), pentane ($C_5H_{12}$), and hexane ($C_6H_{14}$). More preferably, the alkane used is n-hexane. The ZSM-5 catalyst is suspended in the alkane in an amount of amount in the range of 10-100 g, 20-80 g, 25-60 g, or 30-40 g of the ZSM-5 catalyst. The alkane is present in an amount of 100-600 mL, 125-500 mL, 200-450 mL, or 300-400 mL. Preferably 30-40 g of the ZSM-5 catalyst is used and preferably 300-400 mL of the solvent is used. The alkane and the ZSM-5 catalyst form a mixture. The mixture is then heated under stirring until reflux at a temperature in the range of 40-100° C., 45-90° C., or 60-80° C. Preferably the mixture is heated under stirring until reflux at a temperature of 60-80° C. After 14-45 minutes a silicon-containing agent is introduced into the mixture. Preferably the silicon-containing agent is tetra ethyl orthosilicate (TEOS) or other siloxide. A solution of the alkoxide is introduced corresponding to a loading of 2-6% wt. %. Silicon dioxide is then introduced into the mixture and the mixture undergoes silylation.

Silylation is carried out for a time period in the range of 30 minutes-4 hours, 45 minutes-3.5 hours, or 1-3 hours at a temperature in the range of 40-100° C., 45-90° C., or 60-80° C. Preferably silylation is carried out in a time period of 1-3 hours at a temperature of 60-80° C. under reflux and stirring to form a sample. Following silylation, excess solvent is removed by evacuation. The sample is dried at a temperature in the range of 40-150° C., 60-125° C., or 80-100° C. for a time period in the range of 18-30 hours, 19-28 hours, or 20-28 hours. Preferably the sample is dried at a temperature of 80-100° C. at a time period of 20-28 hours. The sample is then calcined in air at a temperature in the range of 200-600° C., 300-550° C., or 400-500° C. at a time period in the range of 1-7 hours, 1.5-6 hours, or 2-6 hours. Preferably the sample is calcined in air at a temperature of 400-500° C. for 2-6 hours with a heating rate of 3-7° C./minute. Silylation treatment is repeated 2-6 times using the same procedure. Preferably silylation treatment is repeated 3 times.

In one embodiment the parent ZSM-5 is modified with a silylating agent (tetraethyl orthosilicate). SiO$_2$ is derived from tetraethyl orthosilicate from the following reaction:

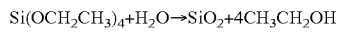

$Si(OCH_2CH_3)_4 + H_2O \rightarrow SiO_2 + 4CH_3CH_2OH$

When tetraethyl orthosilicate is exposed to water, a reaction occurs in which silicon dioxide and ethanol are formed. The silicon dioxide contacts the ZSM-5 and forms a composition in which a silicon-containing group is bonded to the surface of the zeolite catalyst.

In one embodiment, after calcination, the deposited silica layer comprises siloxane bonds (Si—O—Si) whereas the zeolite comprises Si—O—Al bonds. The difference in bonds results in variation of the bond length and angles between the silica layer and the zeolite framework. Preferably the bond length is in the range of 161-190 pm. The siloxane bond of the silica layer protrudes into the pore and the pore opening is reduced because of the siloxane bond. This leads to diffusion resistance for meta- and ortho-isomers with easy transition access for the para-isomer.

In one embodiment the silylating agent, tetraethyl orthosilicate, deposits across the external surface area of the catalyst, preferably the entire catalyst, as a thin layer and covers the non-selective active sites of the catalyst. The internal structure of the catalyst remains unchanged and unaltered by the silylating agent.

In another embodiment the silylating agent does not penetrate the external surface of the catalyst.

The product formed by the described method is preferably at least 90% of the para isomer of the dialkylbenzene. More preferably the para-isomer displays independent selectivity of greater than or equal to 95% para-xylene, greater than or equal to 99% para-ethyltoluene, and greater than or equal to 94% para-diethylbenzene when the reaction temperature is 250° C. Most preferably the para-isomer displays independent selectivity greater than or equal to 100% para-xylene, greater than or equal to 100% para-ethyltoluene, and greater than or equal to 95% para-diethylbenzene when the reaction temperature is 250° C.

The catalyst used for the purpose of simultaneously producing p-X, p-ET, and p-DEB is based on ZSM-5 zeolite which has been silanated by a multi-step process. For chemical liquid deposition, a 30-40 g ZSM-5 catalyst was suspended in 300-400 ml of n-hexane and the mixture was heated under stirring until reflux at 60-80° C. After 15-45 minutes, tetra ethyl orthosilicate (TEOS) solution corresponding to a loading of 2-6 wt. % SiO$_2$ was introduced into the mixture. Silylation was continued for a period of 1-3 hours at 60-80° C. under reflux and stirring. Excess n-hexane was removed by evacuation. Finally the sample was dried at 80-100° C. for 20-28 hours and calcined in air at 400-500° C. for 2-6 hours, with a heating rate of 3-7° C./min. Silylation treatment was repeated three times using the same procedure.

In one embodiment, referring to FIG. 1, broad steps in a method for simultaneously producing p-X, p-ET, and p-DEB from ethylbenzene and methanol are illustrated. FIG. 1 is an illustration of a flow diagram for the simultaneous production of p-X, p-ET, and p-DEB. These steps can include:

Step 1—Providing a Short Contact Fluidized-Bed Reactor:

A riser simulator or fast fluidized-bed reactor which includes a reaction chamber, a gas inlet and a gas outlet can be used. The reactor contains a metallic gasket that seals the two chambers with an impeller located in the upper section. Upon rotation of the shaft, gas is forced outward from the center of the impeller towards the walls. This creates a lower pressure in the central region of the impeller thus inducing flow of gas upward through the catalysts chamber from the bottom of the reactor annular region where the pressure is slightly higher. The impeller provides a fluidized-bed of catalyst particles as well as intense gas mixing inside the reactor by fluidized gas. In general, the reactor should allow homogenous mixing of solid catalyst in the fluidized form and the reactant in vapor form for the short contact reaction time. The reaction times can be from 10 to 30 seconds with preferred time as 20 seconds.

Step 2—Providing a Finely-Powdered Catalyst in the Fluidized-Bed Reactor:

The catalyst can include one of the different zeolites selected from ZSM-5, ZSM-11, ZSM-12, ZSM-22, or ZSM-23. The silica to alumina (SiO$_2$:Al$_2$O$_3$) molar ratio is in the range of 50-300, 55-250, 60-200, or 100-150. Preferably the catalyst is the ZSM-5 zeolite with a SiO$_2$:Al$_2$O$_3$ molar ratio of either 80 or 280. The catalyst is modified by repeated silylation. The number of silylations may be from 2 to 6. Preferably the catalyst is silylated 3 times. The catalyst is preferred to be in the finely powdered form in order to facilitate easy fluidization.

Step 3—Heating the Catalyst to Reaction Temperature:

Preferably the reactor is equipped with a heating facility in order to attain near isothermal conditions inside the reactor at required reaction temperatures in the range of 250 to 450° C. Preferably the temperature inside the reactor is 300° C.

Step 4—Reacting the Feedstock Stream Containing Ethylbenzene with an Alkylating Agent, Preferably Methanol:

The reaction of a feedstock stream with an alkylating agent occurs inside a fluidized-bed reactor. The feedstock stream contains ethylbenzene and an alkylating agent. The alkylating agent may be any of the following including but not limited to ethanol, methanol, propanol, and butanol. Preferably methanol is used as the alkylating agent. The required reaction temperatures may be in the range of 250 to 450° C. Preferably the reaction occurs at 300° C. The required pressure is preferably in the range of 0.1 to 5 atm, with preferred pressure being 1 atm.

Step 5—Separating the Product Stream by Conventional Distillation and Recycling the Unconverted Feedstock:

This step is achieved in a product separator unit (using one or more fractionators) by conventional fractional distillation method to separate the product species according to their boiling points. The boiling points of p-xylene, p-ET and p-DEB are 138, 162, and 184° C., respectively.

EXAMPLES

The disclosure is described in examples by way of exemplification, and not for purpose of limitation. The catalyst used in these examples is an exemplary embodiment only, and is not intended to limit the general description of the silylated ZSM-zeolite catalyst as described above.

Example 1

A ZSM-5 catalyst with SiO$_2$:Al$_2$O$_3$ molar ratio of 80 in parent and silylated form was tested for alkylation reaction using ethylbenzene and methanol as feed mixture in a molar ratio of 1:1 to demonstrate its effectiveness for ethylbenzene conversion and simultaneous production of p-X, p-ET, and p-DEB. A sample of 0.8 g catalyst was weighed and loaded into the riser simulator basket. The system was then sealed and tested for any pressure leaks by monitoring the pressure changes in the system. Catalyst was activated for 15 minutes at 620° C. in a stream of argon. The pretreatment of the catalyst was carried out using a mixture of ethylbenzene and methanol (200 microliter) in a molar ratio of 1:1 at reaction temperatures of 250-400° C., for a reaction time of 20 s. Thereafter, the system was purged with argon for 10 min before the start of the reaction.

Catalytic experiments were carried out in the riser simulator with a 200 microliter of feed mixture injected directly into the reactor via loading syringe, for reaction times of 5, 10 and 20 s at 300° C. reaction temperature. Also, the reactor was heated to the desired reaction temperature. The vacuum box was also heated to 250° C. and evacuated to a pressure of 0.5 psi to prevent any condensation of hydrocarbons inside the box. The heating of the riser simulator was conducted under continuous flow of inert gas (argon), and it usually takes a few hours until thermal equilibrium is finally attained.

The products were analyzed in an Agilent 6890N gas chromatograph with a flame ionization detector and a capillary column of INNOWAX, 60-m cross-linked methyl silicone with an internal diameter of 0.32 mm. The product composition is presented in Table 1 along with selectivity of p-X, p-ET, and p-DEB obtained. Table 1 is presented below.

Example 2

A ZSM-5 catalyst with $SiO_2:Al_2O_3$ molar ratio of 280 in parent and silylated form was tested for alkylation reaction using an ethylbenzene and methanol as feed mixture in a molar ratio of 1:1 to demonstrate its effectiveness for ethylbenzene conversion and simultaneous production of p-X, p-ET, and p-DEB. A sample of 0.8 g catalyst was weighed and loaded into the riser simulator basket. The system was then sealed and tested for any pressure leaks by monitoring the pressure changes in the system. Catalyst was activated for 15 minutes at 620° C. in a stream of argon. The pretreatment of the catalyst was carried out using a mixture of ethylbenzene and methanol (200 microliter) in a molar ratio of 1:1 at reaction temperatures of 250-400° C., for a reaction time of 20 s. Thereafter, the system was purged with argon for 10 min before the start of the reaction.

Catalytic experiments were carried out in the riser simulator with a 200 microliter of fee mixture injected directly into the reactor via loading syringe, for reaction times of 5, 10 and 20 s at 300° C. reaction temperature. Also, the reactor was heated to the desired reaction temperature. The vacuum box was also heated to 250° C. and evacuated to a pressure of 0.5 psi to prevent any condensation of hydrocarbons inside the box. The heating of the riser simulator was conducted under continuous flow of inert gas (argon), and it usually takes a few hours until thermal equilibrium is finally attained.

The products were analyzed in an Agilent 6890N gas chromatograph with a flame ionization detector and a capillary column of INNOWAX, 60-m cross-linked methyl

TABLE 1

| | Parent Catalyst: ZSM-5(80) | | | | Silylated Catalyst: ZSM-5(80)-3X | | | |
|---|---|---|---|---|---|---|---|---|
| | 250° C. | 300° C. | 350° C. | 400° C. | 250° C. | 300° C. | 350° C. | 400° C. |
| Product Composition (wt. %) | | | | | | | | |
| $C_1$-$C_4$ Hydrocarbons | 2.40 | 4.09 | 6.71 | 10.36 | 2.91 | 4.14 | 5.98 | 8.72 |
| Methanol | 1.48 | 1.66 | 1.89 | 2.11 | 2.52 | 2.23 | 2.00 | 1.91 |
| Benzene | 1.94 | 7.58 | 10.75 | 17.52 | 0.66 | 2.90 | 7.26 | 12.78 |
| Toluene | 1.22 | 5.31 | 7.66 | 12.69 | 0.43 | 2.22 | 5.36 | 8.14 |
| Ethylbenzene | 71.84 | 52.95 | 45.71 | 38.47 | 89.64 | 80.11 | 69.84 | 60.69 |
| ortho-Xylene | 0.30 | 0.72 | 1.15 | 1.66 | 0.00 | 0.00 | 0.00 | 0.00 |
| meta-Xylene | 0.78 | 1.74 | 2.69 | 3.75 | 0.00 | 0.00 | 0.11 | 0.27 |
| para-Xylene | 0.48 | 0.88 | 1.29 | 1.78 | 0.44 | 1.56 | 3.07 | 3.62 |
| iso-Propylbenzene | 0.00 | 0.10 | 0.14 | 0.21 | 0.00 | 0.00 | 0.00 | 0.00 |
| ortho-Ethyltoluene | 0.62 | 0.99 | 1.21 | 1.04 | 0.00 | 0.00 | 0.00 | 0.00 |
| meta-Ethyltoluene | 5.65 | 5.67 | 5.56 | 3.90 | 0.00 | 0.00 | 0.00 | 0.00 |
| para-Ethyltoluene | 2.69 | 2.43 | 2.38 | 1.65 | 1.73 | 2.97 | 3.00 | 2.13 |
| orhto-Diethylbenzene | 0.79 | 1.06 | 1.05 | 0.50 | 0.00 | 0.00 | 0.00 | 0.00 |
| meta-Diethylbenzene | 6.43 | 9.90 | 7.94 | 2.90 | 0.09 | 0.45 | 0.42 | 0.29 |
| para-Diethylbenzene | 3.37 | 4.81 | 3.76 | 1.32 | 1.58 | 3.43 | 2.96 | 1.45 |
| Conversion (wt. %) | | | | | | | | |
| Ethylbenzene | 21.64 | 42.23 | 50.14 | 58.03 | 2.21 | 12.61 | 23.81 | 33.79 |
| Grouped Amounts (wt. %) | | | | | | | | |
| Xylenes | 1.56 | 3.34 | 5.14 | 7.19 | 0.44 | 1.56 | 3.19 | 3.88 |
| Ethyltoluenes | 8.97 | 9.09 | 9.16 | 6.60 | 1.73 | 2.97 | 3.00 | 2.13 |
| Diethylbenzenes | 10.59 | 15.77 | 12.75 | 4.71 | 1.67 | 3.88 | 3.38 | 1.74 |
| Selectivity (%) | | | | | | | | |
| para-Xylene | 30.79 | 26.24 | 25.12 | 24.75 | 100.00 | 100.00 | 96.46 | 93.15 |
| para-Ethyltoluene | 30.03 | 26.68 | 26.01 | 25.06 | 100.00 | 100.00 | 100.00 | 100.00 |
| para-Diethylbenzene | 31.82 | 30.51 | 29.48 | 27.92 | 94.41 | 88.31 | 87.54 | 83.39 |

The results show that the selectivity of p-X, p-ET, and p-DEB at 250° C. was 100%, 100% and 94%, respectively. However, with the increase in reaction temperature, the selectivity of p-X and p-DEB decreased to 93% and 83%, respectively.

silicone with an internal diameter of 0.32 mm. The product composition is presented in Table 1 along with selectivity of p-X, p-ET, and p-DEB obtained. The product composition is presented in Table 2 along with selectivity of p-X, p-ET, and p-DEB obtained. Table 2 is presented below.

TABLE 2

| | Parent Catalyst: ZSM-5(280) | | | | Silylated Catalyst: ZSM-5(280)-3X | | | |
|---|---|---|---|---|---|---|---|---|
| | 250° C. | 300° C. | 350° C. | 400° C. | 250° C. | 300° C. | 350° C. | 400° C. |
| Product Composition (wt. %) | | | | | | | | |
| $C_1$-$C_4$ Hydrocarbons | 4.20 | 3.90 | 4.69 | 7.49 | 0.94 | 2.33 | 4.61 | 6.60 |
| Methanol | 1.95 | 1.20 | 1.12 | 1.40 | 6.90 | 4.30 | 3.37 | 2.09 |
| Benzene | 0.30 | 1.15 | 4.23 | 9.77 | 0.14 | 0.70 | 2.24 | 4.85 |
| Toluene | 0.28 | 1.20 | 3.77 | 8.07 | 0.11 | 0.76 | 2.36 | 4.71 |
| Ethylbenzene | 84.82 | 75.35 | 60.31 | 48.55 | 90.99 | 86.90 | 78.35 | 70.89 |
| ortho-Xylene | 0.00 | 0.22 | 0.57 | 1.09 | 0.00 | 0.00 | 0.08 | 0.17 |
| meta-Xylene | 0.15 | 0.54 | 1.42 | 2.69 | 0.00 | 0.08 | 0.19 | 0.40 |
| para-Xylene | 0.41 | 1.21 | 1.95 | 2.21 | 0.00 | 0.61 | 1.75 | 2.98 |
| iso-Propylbenzene | 0.00 | 0.00 | 0.12 | 0.18 | 0.00 | 0.05 | 0.08 | 0.10 |
| ortho-Ethyltoluene | 0.08 | 0.07 | 0.17 | 0.53 | 0.00 | 0.06 | 0.03 | 0.00 |
| meta-Ethyltoluene | 1.32 | 3.36 | 4.94 | 5.09 | 0.00 | 0.00 | 0.00 | 0.00 |
| para-Ethyltoluene | 5.46 | 4.92 | 4.04 | 3.09 | 0.81 | 2.63 | 3.62 | 4.39 |
| orhto-Diethylbenzene | 0.14 | 0.30 | 0.40 | 0.59 | 0.00 | 0.00 | 0.02 | 0.00 |
| meta-Diethylbenzene | 0.19 | 2.26 | 5.91 | 5.42 | 0.00 | 0.15 | 0.29 | 0.25 |
| para-Diethylbenzene | 0.71 | 4.32 | 6.36 | 3.83 | 0.11 | 1.43 | 3.00 | 2.56 |
| Conversion (wt. %) | | | | | | | | |
| Ethylbenzene | 7.47 | 17.80 | 34.21 | 47.04 | 0.75 | 5.21 | 14.54 | 22.67 |
| Grouped Amounts (wt. %) | | | | | | | | |
| Xylenes | 0.57 | 1.98 | 3.94 | 5.99 | 0.00 | 0.69 | 2.03 | 3.54 |
| Ethyltoluenes | 6.86 | 8.35 | 9.14 | 8.72 | 0.81 | 2.69 | 3.65 | 4.39 |
| Diethylbenzenes | 1.03 | 6.87 | 12.66 | 9.84 | 0.11 | 1.59 | 3.31 | 2.81 |
| Selectivity (%) | | | | | | | | |
| para-Xylene | 72.95 | 61.43 | 49.55 | 36.87 | 100.00 | 88.80 | 86.54 | 84.10 |
| para-Ethyltoluene | 79.64 | 58.93 | 44.15 | 35.49 | 100.00 | 97.73 | 99.22 | 100.00 |
| para-Diethylbenzene | 68.65 | 62.82 | 50.20 | 38.97 | 100.00 | 90.24 | 90.58 | 91.15 |

The results show that the selectivity of p-ET, and p-DEB at 250° C. was 100%. However, with the increase in reaction temperature, the selectivity of p-X and p-DEB decreased to 84% and 91%, respectively.

Figure 2:
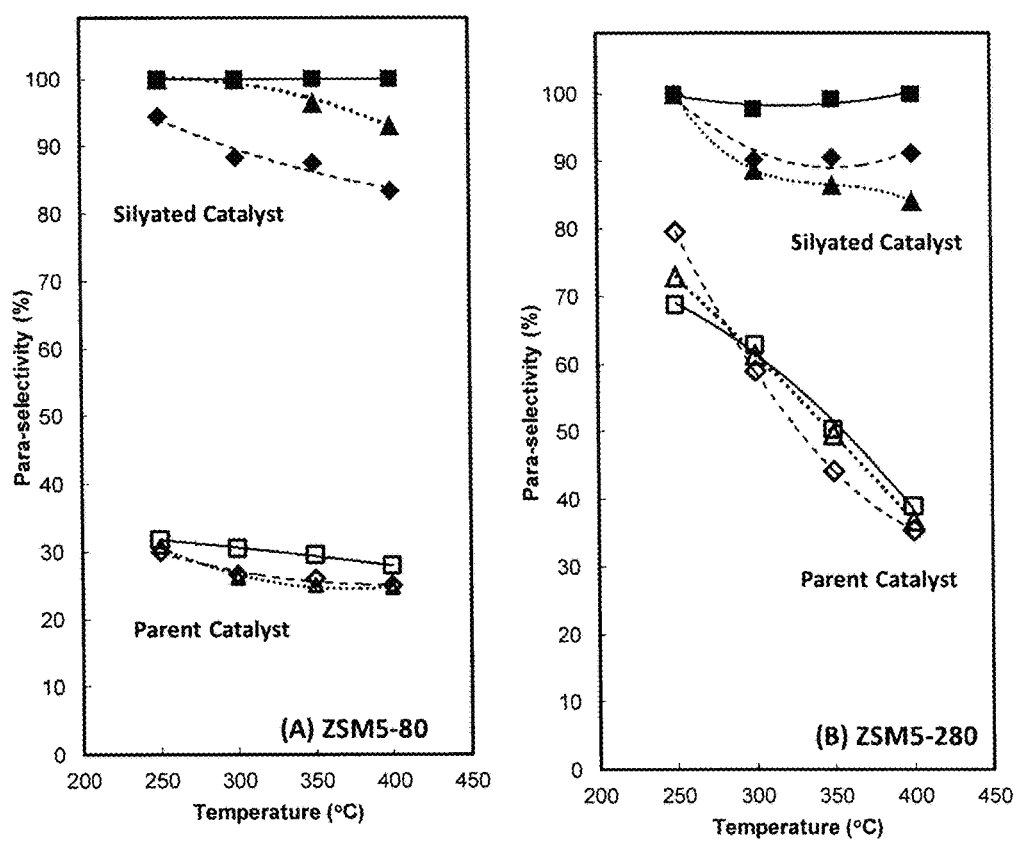
FIG. 2 illustrates two graphs (A) and (B) illustrating the selectivity to p-X, p-ET, and p-DEB obtained by parent and silylated forms of ZSM5-80 and ZSM5-280.

The enhancement in selectivity of p-X, p-ET, and p-DEB obtained by silylation of the catalyst is further clarified by plotting the results from Example 1 and Example 2 in FIG. 2. FIG. 2 is two graphs illustrating the selectivity to p-X (Δ), p-ET (□), and p-DEB (◇) obtained by parent (empty symbols) and silylated (filled symbols) forms of ZSM-5(80) (A) and ZSM-5(280) (B). A method for converting a mixture of ethylbenzene and methanol to p-X, p-ET, and p-DEB include a reactant feedstock source configured to provide a reactant gas flow; a reactor configured to provide fluidization for the catalyst; and a catalyst configured to contact the reactant feedstock.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:

1. A method for production of para-dialkylbenzenes comprising:
    contacting, at a temperature of from 245 to 255° C. and a reaction time of from 5 to 20 seconds, a silylated solid ZSM-5 zeolite catalyst in fluidized bed form in a fluidized-bed reactor with a reactant comprising ethylbenzene and methanol to alkylate the ethylbenzene present in the reactant to form a para-dialkylbenzene mixture comprising para-xylene, para-ethyltoluene and para-diethylbenzene,
    wherein the contacting forms the para-dialkylbenzene mixture with a para selectivity of from 95 to 100% for the para-xylene, a para selectivity of from 90 to 100% for the para-ethyltoluene, and a para selectivity of from 80 to 100% the para-diethylbenzene; and
    wherein the silylated solid ZSM-5 zeolite catalyst has a $SiO_2$:$Al_2O_3$ ratio of 80 and consists of Si, $SiO_2$ and $Al_2O_3$.

2. The method of claim 1 further comprising separating one or more para-dialkylbenzenes from the para-dialkylbenzene mixture by fractional distillation.

3. The method of claim 1 wherein the ethylbenzene and the methanol in the reactant are combined in a molar ratio of 1:0.1 to 1:5.

4. The method of claim 1 wherein the silylated solid ZSM-5 zeolite catalyst is obtained by silylating a ZSM-5 zeolite with a silicon-containing agent at least three times.

5. The method of claim 1 wherein the reactant comprising the ethylbenzene and the methanol is in vapor form.

6. The method of claim 1 wherein the reactant comprises the ethylbenzene and the methanol in a molar ratio of 1:1.

7. A method for production of a para-dialkylbenzene mixture, comprising:
    contacting, at a temperature of from 250 to 400° C. and a reaction time of from 5 to 20 seconds, a silylated solid ZSM-5 zeolite catalyst in fluidized bed form in a fluidized-bed reactor with a reactant comprising ethylbenzene and methanol to alkylate the ethylbenzene present in the reactant to form the para-dialkylbenzene mixture comprising para-xylene, para-ethyltoluene, and para-diethylbenzene, wherein the contacting forms the para-dialkylbenzene mixture with a para selectivity of from 95 to 100% for the para-xylene, a para selectivity of from 90 to 100% for the para-ethyltoluene, and a para selectivity of from 80 to 100% the para-diethylbenzene; and wherein the silylated solid ZSM-5 zeolite catalyst has a $SiO_2:Al_2O_3$ ratio of 80 and consists of Si, $SiO_2$ and $Al_2O_3$.

* * * * *